US008672836B2

(12) United States Patent
Higgins et al.

(10) Patent No.: US 8,672,836 B2
(45) Date of Patent: Mar. 18, 2014

(54) METHOD AND APPARATUS FOR CONTINUOUS GUIDANCE OF ENDOSCOPY

(75) Inventors: William E. Higgins, State College, PA (US); Scott A. Merritt, Ridgecrest, CA (US); Lav Rai, State College, PA (US); Jason D. Gibbs, State College, PA (US); Kun-Chang Yu, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 4179 days.

(21) Appl. No.: 12/022,620

(22) Filed: Jan. 30, 2008

(65) Prior Publication Data

US 2008/0207997 A1  Aug. 28, 2008

Related U.S. Application Data

(60) Provisional application No. 60/887,462, filed on Jan. 31, 2007.

(51) Int. Cl.
*A61B 1/04* (2006.01)
*A61B 1/00* (2006.01)
*G09G 5/00* (2006.01)
*G06T 15/10* (2011.01)

(52) U.S. Cl.
USPC .......... 600/117; 600/114; 600/109; 345/630; 345/427

(58) Field of Classification Search
USPC ......... 600/117, 111, 103, 109, 417, 118, 433; 345/427, 630, 424; 348/65, 45; 606/21
See application file for complete search history.

(56) References Cited

U.S. PATENT DOCUMENTS 4,791,934 A  12/1988 Brunnett
5,740,802 A  4/1998 Nafis et al.
(Continued)

FOREIGN PATENT DOCUMENTS

EP  1681011  7/2006
JP  2003265408  9/2003
(Continued)

OTHER PUBLICATIONS

Deligianni, F., A. Chung, and G. Yang. "Patient-specific bronchoscope simulation with $pq$-space-based 2D/3D registration." Computer Aided Surgery, vol. 9, No. 5, p. 215-226 (2004).

(Continued)

*Primary Examiner* — John P Leubecker
*Assistant Examiner* — Ronald D Colque
(74) *Attorney, Agent, or Firm* — Gifford, Krass, Sprinkle, Anderson & Citkowski, P.C.

(57) ABSTRACT

Methods and apparatus provide continuous guidance of endoscopy during a live procedure. A data-set based on 3D image data is pre-computed including reference information representative of a predefined route through a body organ to a final destination. A plurality of live real endoscopic (RE) images are displayed as an operator maneuvers an endoscope within the body organ. A registration and tracking algorithm registers the data-set to one or more of the RE images and continuously maintains the registration as the endoscope is locally maneuvered. Additional information related to the final destination is then presented enabling the endoscope operator to decide on a final maneuver for the procedure. The reference information may include 3D organ surfaces, 3D routes through an organ system, or 3D regions of interest (ROIs), as well as a virtual endoscopic (VE) image generated from the precomputed data-set. The preferred method includes the step of superimposing one or both of the 3D routes and ROIs on one or both of the RE and VE images. The 3D organ surfaces and routes may correspond to the surfaces and paths of a tracheobronchial airway tree extracted, for example, from 3D MDCT images of the chest.

31 Claims, 7 Drawing Sheets

(56) References Cited

U.S. PATENT DOCUMENTS

| | | |
|---|---|---|
| 5,748,767 A | 5/1998 | Raab |
| 5,765,561 A | 6/1998 | Chen et al. |
| 5,776,050 A | 7/1998 | Chen et al. |
| 5,782,762 A | 7/1998 | Vining |
| 5,792,147 A | 8/1998 | Evans et al. |
| 5,830,145 A | 11/1998 | Tenhoff |
| 5,891,034 A | 4/1999 | Bucholz |
| 5,901,199 A | 5/1999 | Murphy et al. |
| 5,920,319 A | 7/1999 | Vining et al. |
| 5,963,612 A | 10/1999 | Navab |
| 5,963,613 A | 10/1999 | Navab |
| 5,971,767 A | 10/1999 | Kaufman et al. |
| 5,999,840 A | 12/1999 | Grimson et al. |
| 6,006,126 A | 12/1999 | Cosman |
| 6,016,439 A | 1/2000 | Acker |
| 6,049,582 A | 4/2000 | Navab |
| 6,083,162 A | 7/2000 | Vining |
| 6,190,395 B1 | 2/2001 | Williams |
| 6,201,543 B1 | 3/2001 | O'Donnell et al. |
| 6,236,743 B1 | 5/2001 | Pratt |
| 6,272,366 B1 | 8/2001 | Vining |
| 6,311,116 B1 | 10/2001 | Lee et al. |
| 6,334,847 B1 | 1/2002 | Fenster et al. |
| 6,343,936 B1 | 2/2002 | Kaufman et al. |
| 6,346,940 B1* | 2/2002 | Fukunaga ............... 345/427 |
| 6,351,573 B1 | 2/2002 | Schneider |
| 6,366,800 B1 | 4/2002 | Vining et al. |
| 6,442,417 B1 | 8/2002 | Shahidi et al. |
| 6,470,207 B1 | 10/2002 | Simon et al. |
| 6,491,702 B2 | 12/2002 | Heilbrun et al. |
| 6,514,082 B2 | 2/2003 | Kaufman et al. |
| 6,535,756 B1 | 3/2003 | Simon et al. |
| 6,546,279 B1 | 4/2003 | Bova et al. |
| 6,593,884 B1 | 7/2003 | Gilboa et al. |
| 6,674,879 B1 | 1/2004 | Weisman et al. |
| 6,675,032 B2 | 1/2004 | Chen et al. |
| 6,694,163 B1 | 2/2004 | Vining |
| 6,771,262 B2 | 8/2004 | Krishnan |
| 6,785,410 B2 | 8/2004 | Vining et al. |
| 6,816,607 B2 | 11/2004 | O'Donnell et al. |
| 6,819,785 B1 | 11/2004 | Vining et al. |
| 6,859,203 B2 | 2/2005 | van Muiswinkel et al. |
| 6,892,090 B2* | 5/2005 | Verard et al. ............... 600/424 |
| 6,909,913 B2 | 6/2005 | Vining |
| 6,920,347 B2 | 7/2005 | Simon et al. |
| 6,928,314 B1 | 8/2005 | Johnson et al. |
| 6,947,584 B1 | 9/2005 | Avila et al. |
| 6,980,682 B1 | 12/2005 | Avinash et al. |
| 7,019,745 B2 | 3/2006 | Goto et al. |
| 7,343,036 B2 | 3/2008 | Kleen et al. |
| 7,623,900 B2* | 11/2009 | Graham et al. ............... 600/407 |
| 7,641,609 B2* | 1/2010 | Ohnishi et al. ............... 600/117 |
| 7,659,912 B2* | 2/2010 | Akimoto et al. ............... 345/619 |
| 7,929,014 B2* | 4/2011 | Akimoto et al. ............... 348/65 |
| 8,049,777 B2* | 11/2011 | Akimoto et al. ............... 348/65 |
| 8,199,984 B2* | 6/2012 | Mori et al. ............... 382/128 |
| 2003/0152897 A1 | 8/2003 | Geiger |
| 2004/0209234 A1 | 10/2004 | Geiger |
| 2004/0252870 A1 | 12/2004 | Reeves et al. |
| 2005/0020878 A1* | 1/2005 | Ohnishi et al. ............... 600/117 |
| 2005/0033117 A1* | 2/2005 | Ozaki et al. ............... 600/109 |
| 2005/0078858 A1 | 4/2005 | Yao et al. |
| 2005/0096526 A1 | 5/2005 | Reinschke |
| 2005/0261550 A1* | 11/2005 | Akimoto et al. ............... 600/117 |
| 2005/0272971 A1* | 12/2005 | Ohnishi et al. ............... 600/101 |
| 2005/0272999 A1 | 12/2005 | Guendel |
| 2006/0084860 A1 | 4/2006 | Geiger et al. |
| 2006/0149134 A1* | 7/2006 | Soper et al. ............... 600/182 |
| 2006/0170765 A1* | 8/2006 | Akimoto et al. ............... 348/45 |
| 2006/0203089 A1* | 9/2006 | Akimoto et al. ............... 348/113 |
| 2007/0142705 A1* | 6/2007 | Ohnishi et al. ............... 600/109 |
| 2007/0173689 A1* | 7/2007 | Ozaki et al. ............... 600/111 |
| 2007/0173694 A1* | 7/2007 | Tsuji et al. ............... 600/146 |
| 2009/0161927 A1* | 6/2009 | Mori et al. ............... 382/128 |

FOREIGN PATENT DOCUMENTS

| | | |
|---|---|---|
| KR | 20020041577 | 6/2002 |
| WO | WO-2006076789 | 7/2006 |

OTHER PUBLICATIONS

Lee, P.Y. and J.B. Moore. "Pose Estimation via Gauss-Newton-on-manifold." 16th International Symposium on Mathematical Theory of Network and System (MTNS), Leuven, 2004.

Hamadeh, A., S. Lavallee, and P. Cinquin. "Automated 3-Dimensional Computed Tomographic and Fluoroscopic Image Registration." Computer Aided Surgery 1998, vol. 3: p. 11-19.

Roberson, R.E. and P.W. Likins. "A Linearization Tool for Use with Matrix Formalisms of Rotational Dynamics." Archive of Applied Mathematics, vol. 37, No. 6: p. 388-392. Nov. 1969.

Asano, F., Y. Matsuno, T. Matsushita, H. Kondo, Yoshio Saito, A. Seko, and Y. Ishihara. "Transbronchial Diagnosis of a Pulmonary Peripheral Small Lesion Using an Ultrathin Bronchoscope with Virtual Bronchoscopic Navigation." Journal of Bronchology (2002), vol. 9, No. 2, p. 108-111.

Geiger, B., G.M. Weiner, K. Schulze, J. Bilger, P. Krebs, K. Wolf, T.Albrecht. "Virtual Bronchoscopy Guidance System for Transbronchial Needle Aspiration." Proceedings of SPIE vol. 5746 (2005).

Grimson, W.E.L., G.J. Ettinger, S.J. White, T. Lozano-Perez, W.M. Wells III, and R. Kikinis. "An Automatic Registration Method for Frameless Stereotaxy, Image Guided Surgery, and Enhanced Reality Visualization." IEEE Transactions on Medical Imaging, Apr. 1996, vol. 15, No. 2, p. 129-140.

Helferty, J.P., A.J. Sherbondy, A.P. Kiraly, and W.E. Higgins. "Computer-based System for the Virtual Endoscopic Guidance of Bronchoscopy." (believed to have been offered for sale, publicly used, and/or published prior to the filing date of this application).

Hopper, K.D., T.A. Lucas, K. Gleeson, J.L. Stauffer, R. Bascom, D. T. Mauger, R. Mahraj. "Transbronchial Biopsy with Virtual CT Bronchoscopy and Nodal Highlighting." Radiology Nov. 2001, vol. 221, No. 2, p. 531-536.

Maurer, C.R., J.M. Fitzpatrick, M.Y. Wang, R.L. Galloway, Jr., R.J. Maciunas, and G.S. Allen. "Registration of Head Volume Images Using Implantable Fiducial Markers." IEEE Transactions on Medical Imaging, Aug. 1997, vol. 16, No. 4, p. 447-462.

McAdams, H.P., P.C. Goodman, and P. Kussin. "Virtual Bronchoscopy for Directing Transbronchial Needle Aspiration of Hilar and Mediastinal Lymph Nodes: A Pilot Study." AJR May 1998, vol. 170, p. 1361-1364.

Merritt, S.A., L. Rai, and W.E. Higgins. "Real-Time CT-Video Registration for Continuous Endoscopic Guidance." (believed to have been offered for sale, publicly used, and/or published prior to the filing date of this application).

Mori, K., T. Enjoji, D. Deguchi, T. Kitasaka, Y. Suenaga, J. Toriwaki, H. Takabatake, and H. Natori. "New image similarity measures for bronchoscope tracking based on image registration between virtual and real bronchoscopic images." (believed to have been offered for sale, publicly used, and/or published prior to the filing date of this application).

Rai, L., S.A. Merritt, and W.E. Higgins. "Real-time Image-based Guidance Method for Lung-Cancer Assessment." (believed to have been offered for sale, publicly used, and/or published prior to the filing date of this application).

Sato, Y., M. Nakamoto, Y. Tamaki, T. Sasama, I. Sakita, Y. Nakajima, M. Monden, and S. Tamura. "Image Guidance of Breast Cancer Surgery Using 3-D Ultrasound Images and Augmented Reality Visualization." IEEE Transactions on Medical Imaging, Oct. 1998, vol. 17, No. 5, p. 681-693.

Schwarz, Y., A.C. Mehta, A. Ernst, F. Herth, A. Engel, D. Besser, and H. D. Becker. "Electromagnetic Navigation during Flexible Bronchoscopy." Respiration 2003, vol. 70, p. 516-522.

Shinagawa, N., K. Yamazaki, Y. Onodera, K. Miyasaka, E. Kikuchi, H. Dosaka-Akita, and M. Nishimura. "CT-Guided Transbronchial Biopsy Using an Ultrathin Bronchoscope with Virtual Bronchoscopic Navigation." Chest, Mar. 2004, vol. 25, p. 1138-1143.

(56) References Cited

OTHER PUBLICATIONS

Shoji, H., K. Mod, J. Sugiyama, Y. Suenaga, J. Toriwaki, H. Takabatake, and H. Natori. "Camera motion tracking of real endoscope by using virtual endoscopy system and texture information." Proceedings of SPIE vol. 4321, p. 122-133 (2001).

Stefansic, J.D., A.J. Herline, Y. Shyr, W.C. Chapman, J.M. Fitzpatrick, B.M. Dawant, and R.L. Galloway, Jr. "Registration of Physical Space to Laparoscopic Image Space for Use in Minimally Invasive Hepatic Surgery." IEEE Transactions on Medical Imaging, Oct. 2000, vol. 19, No. 10, p. 1012-1023.

Turcza, P. and M. Duplaga. "Navigation Systems Based on Registration of Endoscopic and CT-derived Virtual Images for Bronchofiberoscopic Procedures." Studies in Health Technology and Informatics, vol. 105, p. 253-263 (2004).

White, C.S., E.A. Weiner, P. Patel, and E.J. Britt. "Transbronchial Needle Aspiration: Guidance with CT Fluoroscopy." Chest 2000, vol. 118, No. 6, p. 1630-1638.

Higgins, W., W.J.T. Spyra, R.A. Karwoski, and E.L. Ritman. "System for Analyzing High-Resolution Three-Dimensional Coronary Angiograms." IEEE Transactions on Medical Imaging, Jun. 1996, vol. 15, No. 3, p. 377-385.

Brady, M.L., W.E. Higgins, K. Ramaswamy. "Interactive navigation inside 3D radiological images." IEEE 1995, p. 33-40.

Higgins, W.E. and K. Ramaswamy. "Toward dynamic visualization for endoscopy simulation." IEEE 1994, p. 700-701.

Bricauit, I., G. Ferretti, and P. Cinquin. "Registration of Real and CT-Derived Virtual Bronchoscopic Images to Assist Transbronchial Biopsy." IEEE Transactions on Medical Imaging, Oct. 1998, vol. 17, No. 5, p. 703-714.

Sherbondy, A.J., A.P. Kiraly, A.L. Austin, J.P. Helferty, S. Wan, J.Z. Turlington, T. Yang, C. Zhang, E.A. Hoffman, and G. McLennan. "Virtual Bronchoscopic approach for combining 3D CT and Endoscopic Video." Proceedings of SPIE 2000, vol. 3978, No. 104.

Helferty, J.P., A.J. Sherbondy, A.P. Kiraly, J.Z. Turlington, E.A. Hoffman, G. McLennan, W.E. Higgins. "Experiments in virtual-endoscopic guidance of bronchoscopy." Proceedings of SPIE 2001, vol. 4321, No. 111.

Helferty, J.P. and W.E. Higgins. "Combined endscopic video tracking and virtual 3D CT registration for surgical guidance." Proceedings of the 2002 International Conference on Image Processing, vol. 2, pp. 961-964.

Higgins, W.E., J.P. Helferty, and D.R. Padfield. "Integrated bronchoscopic video tracking and 3D CT registration for virtual bronchoscopy." Proceedings of SPIE 2003, vol. 5031, No. 80.

Kiraly, A.P., J.P. Helferty, E.A. Hoffman, G. McLennan, W.E. Higgins. "Three-dimensional path planning for virtual bronchoscopy." IEEE Transactions on Medical Imaging 2004 vol. 23, No. 11, pp. 1365-1379.

Helferty, J.P., E.A. Hoffman, G. McLennan, W.E. Higgins. "CT-video registration accuracy for virtual guidance of bronchoscopy." Proceedings of SPIE 2004, vol. 5369, pp. 150-164.

Higgins, W.E., L. Rai, S.A. Merritt, K. Lu, N. T. Linger, and K.C. Yu. "3D image fusion and guidance for computer-assisted bronchoscopy." Proceedings of SPIE 2005, vol. 6016.

Asano, F., Y Matsuno, N. Shinagawa, K. Yamazaki, T. Suzuki, T. Ishida, and H. Moriya. "A Virtual Bronchoscopic Navigation System for Pulmonary Peripheral Lesions." Chest 2006, vol. 130, No. 2, pp. 559-566.

Kukuk, M. "Modeling the Internal and External Constraints of a Flexible Endoscope for Calculating its Workspace: Application in Transbronchial Needle Aspiration Guidance." Proceedings of SPIE 2002, vol. 4681, pp. 539-550.

Gibbs, J.D. and W.E. Higgins. "3D Path Planning and Extension for Endoscopic Guidance." Proceedings of SPIE 2007, vol. 6509.

Mori, K., S. Ema, T. Kitasaka, Y. Mekada, I. Ide, H. Murase, Y. Suenaga, H. Takabatake, M. Mori, and H. Natori. "Automated Nomenclature of Bronchial Branches Extracted from CT Images and its Application to Biopsy Path Planning in Virtual Bronchoscopy." Medical Image Computing and Computer-Assisted Intervention 2005, Lecture Notes in Computer Science 3750, pp. 854-861.

* cited by examiner

METHOD AND APPARATUS FOR CONTINUOUS GUIDANCE OF ENDOSCOPY

REFERENCE TO RELATED APPLICATION

This application claims priority from U.S. Provisional Patent Application Ser. No. 60/887,462, filed Jan. 31, 2007, the entire content of which is incorporated herein by reference.

GOVERNMENT SPONSORSHIP

This invention was made with government support under Grant No. CA074325, awarded by The National Institutes of Health. The Government has certain rights in the invention.

BACKGROUND OF THE INVENTION

Flexible endoscopy is a class of minimally-invasive procedures wherein a flexible device is maneuvered through the body's existing hollow organs (e.g., tracheobronchial airway tree, colon, sinuses) in order to perform diagnosis or deliver treatment.[1,2] Endoscopy reduces and often eliminates the need for incisions, thereby reducing patient risk and recovery time. Flexible endoscopy is therefore preferable to more invasive surgeries, which typically require an incision large enough for the physician to directly view and manipulate the target operating region.

Endoscopy may be used, for example, in the chest, where routine and relatively low-risk bronchoscopic biopsies can replace transthoracic biopsies that carry the risk of pneumothorax.[1,3,4] Similarly, flexible endoscopy may be used in the heart to facilitate insertion of cardiac pacemaker leads,[5] in the nasal and sinus passages to assist in diagnoses,[6] and in the colon to detect and treat colonic polyps.[7]

The typical workflow of an endoscopic procedure consists of two phases: Phase I, Pre-operative planning; and Phase II, Endoscopy. During Phase I, a three-dimensional (3D) volumetric image—typically acquired by a multi-detector computed tomography (MDCT) or magnetic resonance imaging (MRI) scanner—is acquired for the anatomy of interest.[8-10] Regions of interest (ROIs), such as lymph nodes, suspicious nodules, polyps, etc., are defined by a physician examining a series of 2D transverse slices of this 3D image. During this phase, the endoscopist also plans a route to each ROI, choosing the approach that allows best access for diagnosis and treatment options.[11]

In standard practice, the MDCT scan is displayed on a computer monitor or x-ray film view panel as a series of transverse-plane slices through the chest. Route planning in this case consists of determining a path from the trachea to a location within the tracheobronchial tree from which the ROI is accessible. In standard practice, this step requires the bronchoscopist to mentally reconstruct the anatomy in 3D to determine the best approach to the ROI. It has been shown, however, that the path is often chosen incorrectly using this approach and that physicians have difficulty in identifying airways in CT slices as early as the second generation.[12,13]

In Phase II, the physician performs the endoscopic procedure. Central to this procedure is the task of navigating the endoscope tip to the previously-defined ROIs, relying on both the live endoscopic video feed as well as the analysis of the 3D image performed in Phase I. This task is difficult for several reasons: 1) the ROIs can lie beyond the walls of the hollow organ and are not visible in the endoscopic video; 2) the endoscopic video is markedly different from the 3D radiologic images in which these ROIs are defined; and 3) endoscopic views from different locations within the organ can be visually indistinguishable.

In bronchoscopy, these difficulties are exacerbated by the complexity of the tracheobronchial airway tree in which the bronchoscope operates. These effects result in navigation errors and are known to contribute to large variations in skill level between different physicians.[14,15] Such errors may also result in missed diagnoses, necessitating invasive and potentially fatal follow-up procedures.[3,4] Previously, image-based and electromagnetic (E/M) guidance techniques have been proposed to aid physicians both in navigation to ROIs and in improving the biopsy accuracy of ROIs.

E/M guidance techniques generate an E/M field around the patient, and locate the bronchoscope using an E/M sensor inserted through the instrument channel of the bronchoscope.[16-21] These techniques require special hardware that adds to the cost of each procedure and limits the type of bronchoscope that can be used. Because the E/M probe occupies the bronchoscope's instrument channel, these techniques are not suitable for the smaller channels present on small-diameter endoscopes designed for pediatric or peripheral lung procedures. Furthermore, the E/M probe must be removed from the channel before performing critical procedural steps (e.g., performing biopsy), leaving the physician without location information. In addition, E/M registration can only locate the bronchoscope relative to an external field. It is therefore susceptible to localization errors in the face of patient breathing motion, shifting of the patient during the procedure or different body position between the 3D scan and the procedure, although recent research has begun to address these problems.[19,21,22]

Image-based guidance techniques rely on volumetric image processing in order to serve as a guidance aid for the physician. Virtual bronchoscopic (VB) guidance techniques present the physician with surface or volumetric renderings of the tracheobronchial airway tree that mimic the appearance of real bronchoscopic (RB) video.[23-27] These techniques rely on a technician to move the virtual bronchoscope in tandem with the physician moving the real bronchoscope, in order to provide the physician with more awareness of location within the airways and with respect to the ROIs. While VB guidance has shown promise to improve performance of bronchoscopic procedures, the VB world and the RB world are not directly linked, leaving the physician to make the final inference. In contrast, virtual-to-real (V-R) registration/tracking methods provide an automated link between the volumetric-image-based VB source and the RB video source.[28-35]

This link reduces user intervention and allows fusion of data between the two sources. However, it has previously been computationally intensive, limiting its use to single-frame or buffered-video applications, and requiring the physician to wait several seconds for each registration result.

SUMMARY OF THE INVENTION

This invention is directed to continuous guidance of endoscopy during a live procedure. A data-set based on 3D image data is pre-computed including reference information representative of a predefined route through a body organ to a final destination. A plurality of live real endoscopic (RE) images are displayed as an operator maneuvers an endoscope within the body organ. Information is presented corresponding to an initial reference location along the predefined route enabling the operator to move the endoscope toward the reference location. A registration and tracking algorithm is invoked that registers the data-set to one or more of the RE images and continuously maintains the registration as the endoscope is locally maneuvered. Information corresponding to another reference location along the predefined route is presented, enabling the endoscope operator to move the endoscope close to this new reference location, and these steps are repeated until the endoscope is within the vicinity of the final destination. Additional information related to the final destination is then presented enabling the endoscope operator to decide on a final maneuver for the procedure.

The reference information may include 3D organ surfaces, 3D routes through an organ system, or 3D regions of interest (ROIs), as well as a virtual endoscopic (VE) image generated from the precomputed data-set. The preferred method includes the step of superimposing one or both of the 3D routes and ROIs on one or both of the RE and VE images. The 3D organ surfaces may correspond to the surfaces of a tracheobronchial airway tree extracted from 3D MDCT images of the chest. The 3D routes may correspond to paths traversing a tracheobronchial airway tree extracted from 3D MDCT images of the chest or traversing other neighboring anatomical structures. The ROIs may represent lymph nodes, suspect tumors, narrowed airways, or any other diagnostically relevant regions.

According to a preferred embodiment, one superimposed route is highlighted and continuously presented to guide the endoscope operator. This registered VE view is displayed synchronously with the live RE video. The method and disclosed system are capable of real-time operation.

DETAILED DESCRIPTION OF THE INVENTION

This invention resides in a system-level approach to guidance of endoscopy, including a complete paradigm for real-time image-based guidance providing a physician with continuously-updated navigational and guidance information.

At least three novel embodiments for guidance of endoscopy are disclosed. Additional elements such as global surface rendering, local cross-sectional views, and pertinent distances provide additional utility to the physician. Phantom results were generated using bronchoscopy performed on a rapid prototype model of a human tracheobronchial airway tree. The system has also been tested in ongoing live human tests. Ten such tests have been performed thus far and focus on bronchoscopic intervention of pulmonary patients using 3D chest CT.

This disclosure presents generally applicable methods, but focuses on the chest and bronchoscopy. In this domain, Phase I centers around acquisition and analysis of an MDCT image, where the ROIs may be lymph nodes, suspect cancer nodules, diffuse infiltrates, airway stent locations, or any other clinically-significant locations.[8,10]

At least three integrated system-level approaches for real-time image-based guidance of endoscopy are described. These approaches present novel guidance strategies and are possible because of fast CT-Video registration engines that we have previously proposed.[36,37] The high speed of these registration engines allows continuous registration of the video at a real-time video frame rate. The approach has general applicability to colonoscopy for the colon, sinoscopy for the sinuses and angioscopy for the vasculature. Phantom and live patient results are also presented.

METHODS

Figure 1:
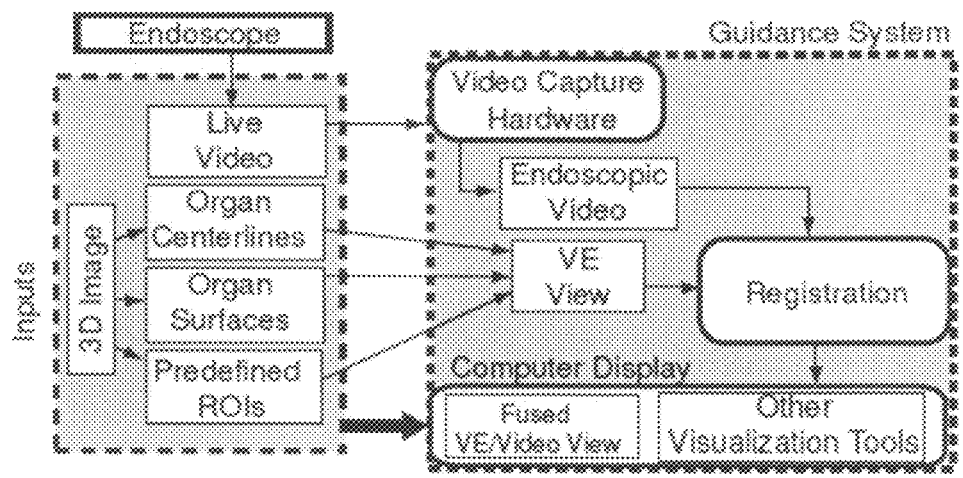
FIG. 1 shows a block diagram of the guidance system, its inputs and the interaction between the system and the physician.

Our approach for continuous guidance of endoscopy relies on multiple inputs, as depicted in FIG. 1. The first of these inputs is the live real endoscopic (RE) video of the anatomy of interest, provided by the endoscope during the endoscopic procedure. The quantity $I_{RE}^{\Theta_j}(i,j)$ denotes the $(i,j)^{th}$ pixel of the $j^{th}$ 2D RE video frame captured from the RE camera's unknown viewpoint $\Theta_j = (x, y, z, \alpha, \beta, \gamma)$ where $(x, y, z)$ denotes the 3D spatial location and $(\alpha, \beta, \gamma)$ denotes the Euler angles specifying the orientation of the RE camera with respect to the radiological image's 3D coordinate axes. The remaining inputs are derived from the 3D image of the anatomy of interest, which is acquired during the preoperative planning phase in advance of the procedure. These inputs include 3D surfaces depicting the interior surface of the hollow organ, the ROIs depicted as 3D regions defined within the scan data, and precomputed 3D paths $P_k$ through the hollow organ to reach these ROIs.

Each path consists of a set of 6D viewpoints known as viewing sites. The $l^{th}$ viewing site of the $k^{th}$ path, denoted by $P_k(l)$, is comprised of $(x, y, z)$ location and orientation parametrized by the Euler angles $(\alpha, \beta, \gamma)$. We work primarily with bronchoscopy, where the endoscopic device is a bronchoscope, and where the 3D surfaces and paths correspond to the surfaces and central axes of the tracheobronchial airway tree, as extracted from a 3D MDCT image of the chest. The ROIs in this domain may be lymph nodes, suspect tumors, narrowed airways, or any other diagnostically relevant regions visible in the 3D MDCT image.

Figure 2:
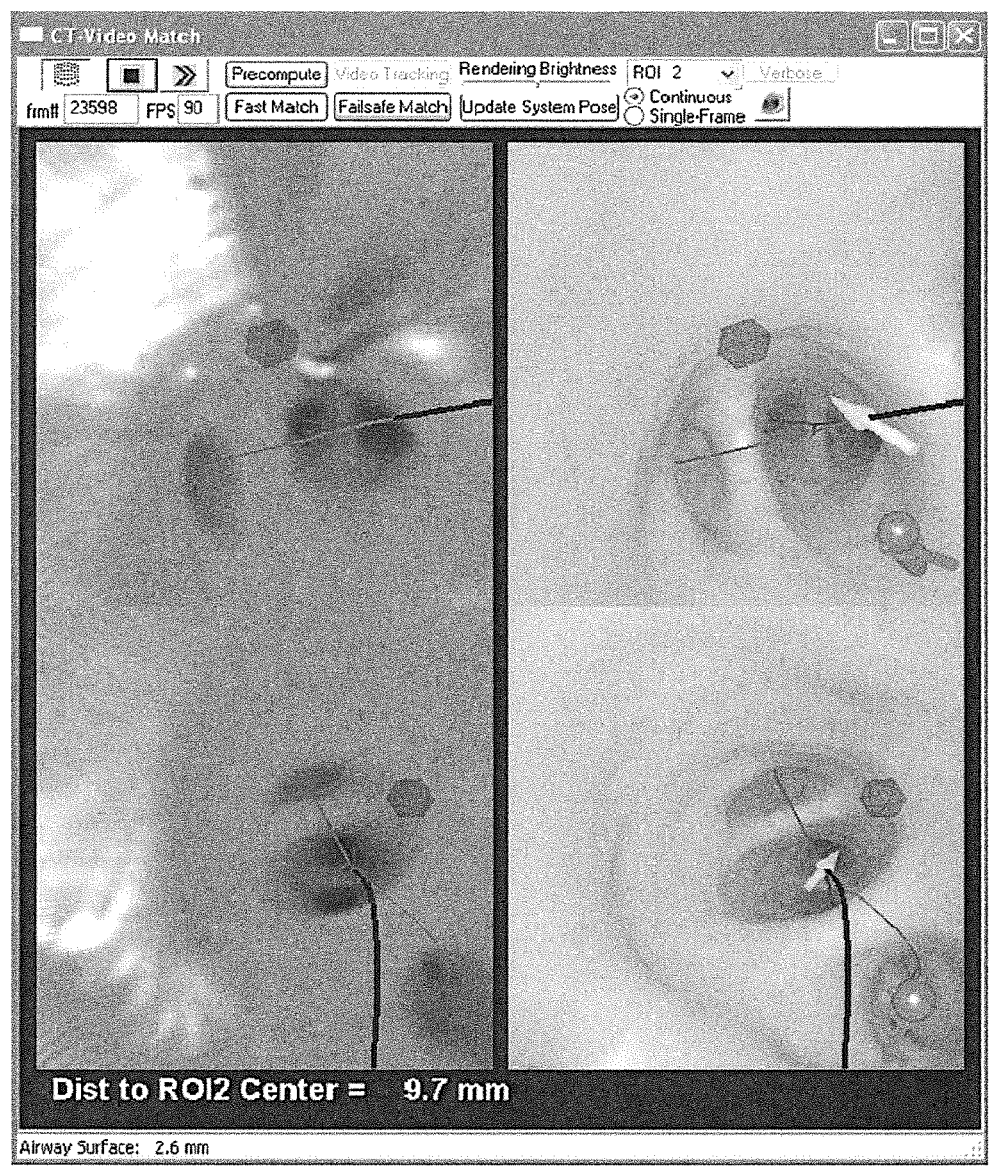
FIG. 2 is an example of a saved registration view.

The guidance system comprises a computer displaying the live real endoscopic (RE) video side-by-side sometimes with a depiction of the interior surface data. The camera parameters—e.g., field of view (FOV)—used to present this surface data match those extracted by calibration of the endoscopic device. Thus, this depiction constitutes a virtual endoscopic (VE) camera. The VE camera can therefore synthesize VE images $I_{VE}^{\Theta_V}$ at arbitrary virtual viewpoint $\Theta_V$ within the CT volume. Let $\hat{\Theta}_f$ denote the registered VE viewpoint that represents the best estimate of the RE camera's unknown viewpoint (i.e., $\hat{\Theta}_f \approx \Theta_f$) and therefore $I_{VE}^{\hat{\Theta}_f}$ denotes the registered VE view. The portions of the 3D path and ROIs visible within the VE camera's FOV can be projected to form a layer image $I_P^{\Theta_V}$ and appear superimposed on the VE view as depicted in FIG. 2 and others. We denote this blending process by the $\oplus$ operator and define the superimposed VE view as $I_{VE+P}^{\Theta_V} \equiv I_{VE}^{\Theta_V} \oplus I_P^{\Theta_V}$. The VE camera can be moved independently of the endoscope, allowing the extracted anatomy to be freely navigated and explored. In FIG. 2, the bottom two panes statically display the RE view $$I_{RE}^{\Theta_{fs}} \oplus I_P^{\hat{\Theta}_{fs}}$$

and registered VE view $$I_{VE+P}^{\hat{\Theta}_{f_s}}$$

from a previous time instant s, while the top two panes dynamically display the current live RE video view $I_{RE}^{\Theta_f} \oplus I_P^{\hat{\Theta}_f}$ and registered VE view $I_{VE+P}^{\hat{\Theta}_f}$. Each view has the 3D paths and ROI overlaid. This saved view is useful for keeping an overview of the local area when performing biopsies.

The above inputs and system provide the basis for three endoscopic guidance strategies. Strategy I centers around registrations performed at discrete decision points (e.g., bifurcations of the airway tree). Each registration presents the physician with the correct path on which to continue in order to reach the ROI and, if close enough, presents the location of the ROI itself. In contrast, continuous registration/tracking is at the core of Strategy II and allows the registered VE view $I_{VE+P}^{\hat{\Theta}_f}$ to be displayed synchronously with the live RE video $I_{RE}^{\Theta_f}$. In order to simplify the view presented to the physician, Strategy III refines upon Strategy II by presenting only the 3D paths and ROIs fused onto the RE video ($I_{RE}^{\Theta_f} \oplus I_P^{\hat{\Theta}_f}$), dispensing altogether with the VE view. The three strategies are integrated; each strategy builds upon the previous one and any combination of these strategies may be used for guidance to a particular ROI. The methods are presented below along with a more concrete step-by-step example for the case of bronchoscopy.

Endoscopic Guidance Strategy I

The goal of Strategy I is to provide guidance at key decision points (e.g, bifurcation points) along the path to each ROI. As such, this method centers on discrete registration/tracking events at each of these decision points. The method proceeds as follows:

1. A VE view $I_{VE+P}^{\Theta_{v_0}}$, displaying the 3D path and ROIs, is presented at an initial reference location $\Theta_{v_0} = P_k(l_0)$ along the path to the current ROI (e.g., main carina for bronchoscopy).
2. The physician moves the endoscope so it is within the vicinity of the VE view.
3. A combined registration/tracking may optionally be invoked, thereby making the virtual 3D space registered to the current viewpoint of the endoscope (i.e., the viewpoint of the RE camera is estimated and the VE camera matches this viewpoint: $\Theta_v = \hat{\Theta}_f$). At this point, the pre-computed 3D path and ROIs may also be superimposed on the RE video frame ($I_{RE}^{\Theta_f} \oplus I_P^{\hat{\Theta}_f}$). The physician may then maneuver and handle the endoscope locally, with the 3D path and ROIs properly adjusting their positions on the superimposed view to account for the local scope movement. Additionally, an instantaneous snapshot of the current registered views may be saved and displayed alongside the continuously-updating VE $I_{VE+P}^{\hat{\Theta}_f}$ and RE $I_{RE}^{\Theta_f} \oplus I_P^{\hat{\Theta}_f}$ views to provide, for example, an overview of the biopsy site before moving close to the surface to perform the biopsy. An example of this saved view is displayed in FIG. 2. As with each of the three strategies, the 3D path and ROIs $I_P^{\hat{\Theta}_f}$ may be toggled at any point to allow unobscured observation of the RE video $I_{RE}^{\Theta_f}$. Alternately, display of the ROI may be automatically suppressed if the endoscope has not reached the local vicinity of the destination.
4. The registration/tracking operation is temporarily halted and the VE camera is moved further along the desired path ($\Theta_{v_i} \leftarrow P_k(l_i)$), closer to the 3D ROI.
5. Steps 2-4 are repeated until the endoscope is within the local vicinity of the destination. The ROI (if previously suppressed) can now appear in order to provide an unambiguous signal that the target location (e.g., the proper local airway branch) has been reached.
6. An additional graphical icon is introduced to confirm that the biopsy site of interest is within the current field of view. Previous works have used transparency-based rendering to fuse an ROI onto a rendered anatomical region such as an airway lumen, but this results in ambiguity in the actual location of the ROI. With the added feature of the icon—an arrow in the case of FIGS. 2 and 6—this ambiguity is eliminated.

Figure 6:
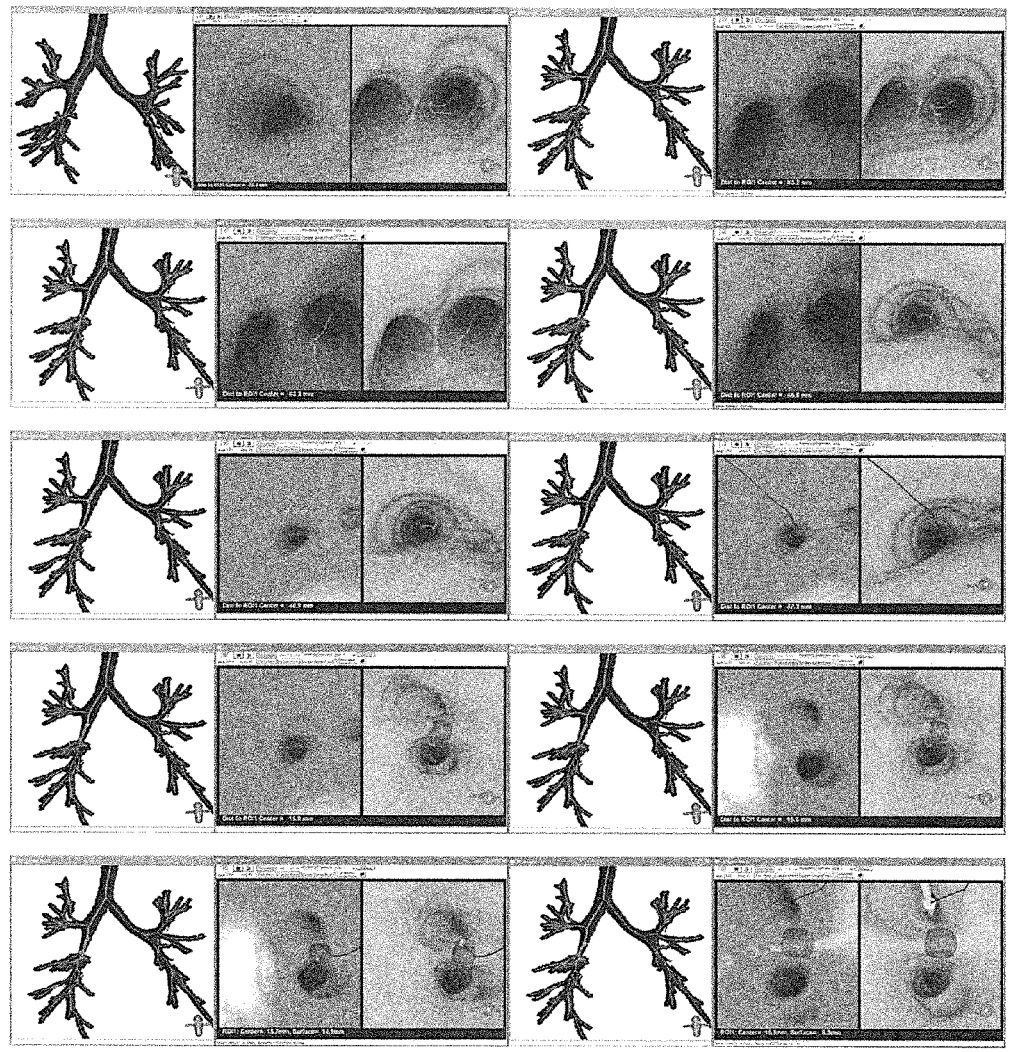
FIG. 6 shows discrete decision points along a path to a region of interest (ROI)

An example of this method is shown in FIG. 6 in the results: (Rows 1-3) show steps 1-4 for the first two decision points. At each of these locations, the ROI is initially suppressed to avoid distraction. Upon arriving at the local vicinity of the destination (Rows 4,5), the 3D ROI and graphical icon appear to unambiguously display the location of the biopsy site. At this point, a saved registration view may be invoked (see FIG. 2) to further increase the physician's confidence in choosing a biopsy location.

Strategy I presents a framework for discrete registrations along a path to an ROI. With the previously-proposed registration/tracking methods,[36,38] these discrete registration events are not only nearly instantaneous, allowing this process to be time-efficient, but also continuously update in real-time to reflect local changes in the viewpoint of the endoscope. This is a major improvement over prior guidance methods, such as those in the references that incorporated discrete static registrations on buffered video frames.[28-35]

Endoscopic Guidance Strategy II

Because registration/tracking methods are already fast enough to allow the VE view to be continuously synchronized with the video, we propose a variant of Strategy I that incorporates continuous registration as an alternative to the discrete registration in step 3. In this alternate strategy, after the initial registration is done (steps 1 and 2 above), registration can be performed continuously on the incoming video: the physician freely moves the endoscope, and the VE view continuously updates, assisting the physician to move the endoscope along the proper path to the ROI. As with Strategy I, display of the ROIs can be suppressed until within the local vicinity of the destination, and the 3D paths and ROIs can be toggled to provide the physician with additional guidance information or with unobscured visualization of the RE video. This alternate framework defines Strategy II.

Figure 3:
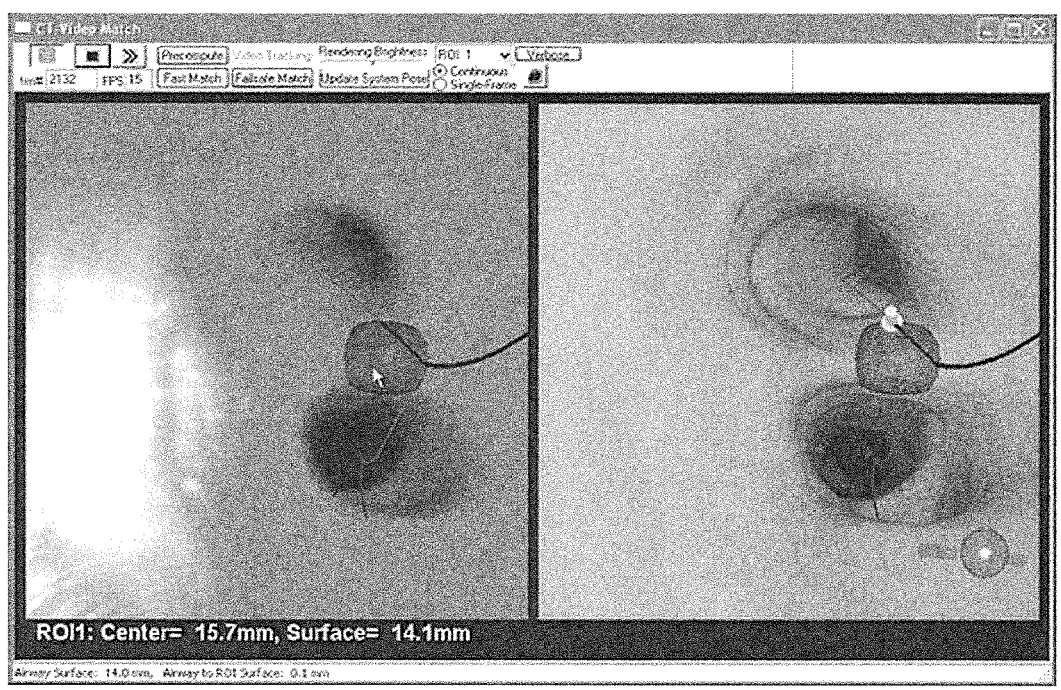
FIG. 3 depicts a guidance Strategy II.

1. A VE view $I_{VE+P}^{\Theta_{v_0}}$, is presented at an initial reference location $\Theta_{v_0} = P_k(l_0)$ along the path to the current ROI.
2. The physician moves the endoscope so it is within the vicinity of the VE view $I_{VE+P}^{\Theta_{v_0}}$.
3. Continuous registration/tracking is activated, thereby making the virtual 3D space registered to the current position of the endoscope (i.e., $\Theta_{v_f} = \hat{\Theta}_f \forall f$). At this point, the 3D path and ROIs (if not suppressed) may optionally be superimposed on the RE video $I_{RE}^{\Theta_f} \oplus I_P^{\hat{\Theta}_f}$ as shown in FIG. 3. During continuous registration, the VE view (right) moves synchronously with the RE video (left). Likewise, the 3D ROI and paths can be superimposed in real-time on the RE video to provide guidance information. Distances to the ROI center and surface are shown in white. In addition, hovering the cursor above the ROI displays distances to the airway and ROI surfaces at that particular point.

4. As the physician moves the endoscope along the proper path to the ROI, the VE view $I_{VE+P}^{\hat{\Theta}_f}$ and RE view $I_{RE}^{\Theta_f} \oplus I_P^{\hat{\Theta}_f}$, both including 3D paths and ROIs (if not suppressed), continuously updates until either the ROI is reached or an unsatisfactory registration result is produced.
5. In the case of an unsatisfactory registration result, continuous registration/tracking is deactivated, the VE view returns to the last known good location along the path ($\Theta_v \leftarrow P_k(l_n)$) and navigation proceeds as normal from step 2.
6. When the endoscope is within the local vicinity of the destination, the ROI (if previously suppressed) now appears superimposed in real-time on the VE and RE views in order to provide an unambiguous signal that the target location (e.g, the proper local airway branch) has been reached.
7. An additional graphical icon is introduced to confirm that the biopsy site of interest is within the current field of view. Previous works have used transparency-based rendering to fuse an ROI onto a rendered anatomical region such as an airway lumen, but this results in ambiguity in the actual location of the ROI, with the added feature of the icon—an arrow in the case of FIGS. 2 and 6—this ambiguity is eliminated.

Endoscopic Guidance Strategy III

Figure 4:
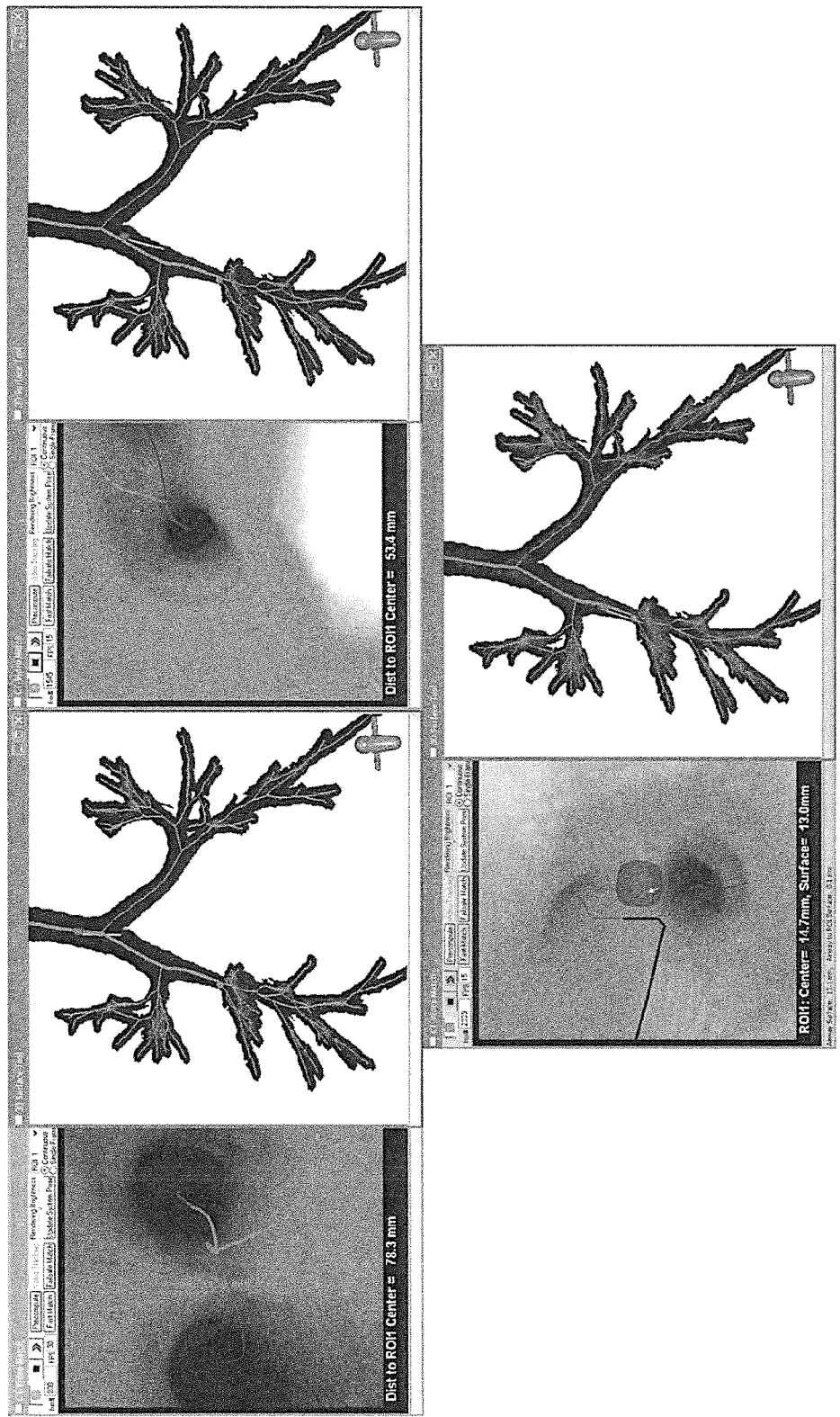
FIG. 4 depicts a guidance Strategy III.

During continuous registration/tracking in Strategy II, there is little information presented by the VE view $I_{VE+P}^{\hat{\Theta}_f}$ that is not already present in the augmented RE video with superimposed paths and ROIs $I_{RE}^{\Theta_f} \oplus I_P^{\hat{\Theta}_f}$. Hence, a variant of Strategy II is to dispense with this unnecessary VE view $I_{VE+P}^{\hat{\Theta}_f}$ during continuous registration and present only the RE video with continuously-updated paths and ROIs superimposed thereon $I_{RE}^{\Theta_f} \oplus I_P^{\hat{\Theta}_f}$, as shown in FIG. 4. As with Strategies I and II, these 3D path and ROI elements may be toggled on/off at any point to allow unobscured inspection of the organ surface in the RE video $I_{RE}^{\Theta_f}$. In FIG. 4, three viewpoints are shown along the path to the ROI. In Strategy III, the VE view is not displayed. Only the live RE view $I_{RE}^{\Theta_f} \oplus I_P^{\hat{\Theta}_f}$ is shown, with path and ROI information $I_P^{\hat{\Theta}_f}$ superimposed on each video frame $I_{RE}^{\Theta_f}$ in real-time. In each case, a colored line indicates the proper path to the ROI. An external rendering of the airway tree is shown next to the RE video pane, indicating the position of the endoscope tip updating in real-time.

1. A VE view $I_{VE+P}^{\Theta_{v_0}}$ is presented at an initial reference location $\Theta_{v_0} = P_k(l_0)$ along the path to the current ROI.
2. The physician moves the endoscope so it is within the vicinity of the VE view $I_{VE+P}^{\Theta_{v_0}}$.
3. Continuous registration/tracking is activated, thereby making the virtual 3D space registered to the current position of the endoscope (i.e., $\Theta_{v_f} = \hat{\Theta}_f \forall f$). At this point, the VE view $I_{VE+P}^{\Theta_v}$ is hidden, and the 3D paths and ROIs (if not suppressed) are superimposed on the RE video $I_{RE}^{\Theta_f} \oplus I_{hu}^{\hat{\Theta}_f}$. Note that in this strategy, because there is no VE view, the 3D paths superimposed on the RE video are critical to guidance. However, they can still be temporarily toggled off to provide unobscured inspection of the RE video $I_{RE}^{\Theta_f}$.
4. As the physician moves the endoscope along the proper path to the ROI, the RE view $I_{RE}^{\Theta_f} \oplus I_P^{\hat{\Theta}_f}$, including the 3D paths and ROIs (if not suppressed) continuously updates until either the target location is reached or an unsatisfactory registration result is produced.
5. In the case of an unsatisfactory registration result, continuous registration/tracking is deactivated, the VE view is restored and displays the last known good location along the path ($\Theta_v \leftarrow P_k(l_n)$). Navigation then proceeds as normal from step 2.
6. When the endoscope is within the local vicinity of the destination, the ROI (if previously suppressed) now appears superimposed in real-time on the RE view $I_{RE}^{\Theta_f} \oplus I_P^{\hat{\Theta}_f}$ in order to provide an unambiguous signal that the target location (e.g., the proper local airway branch) has been reached.
7. In order to eliminate the ambiguity in the location of the ROI, an additional graphical icon (e.g., an arrow similar to those in FIGS. 2 and 6) may optionally be introduced and blended with the RE view $I_{RE}^{\Theta_f} \oplus I_P^{\hat{\Theta}_f}$ to confirm that the biopsy site of interest is within the current field of view.

Method Comments

The above three methods provide the basic strategies for guidance of endoscopy. At times prior to and during endoscopy, it is useful to provide the physician with additional information, which updates continuously or with each discrete registration. Distances may be displayed, including: 1) the distance from the endoscope tip to the ROI center; and 2) minimum distance from endoscope tip to the ROI surface. Hovering the mouse over a point in the VE view $I_{VE+P}^{\Theta_v}$ or registered RE view also $I_{RE}^{\Theta_f} \oplus I_P^{\hat{\Theta}_f}$ provides additional distances specific to that point. These include: 1) the distance from endoscope tip to the organ surface; and 2) the distance from the endoscope tip to the ROI surface. Our system provides a global 3D surface renderer to display a global exterior view of the organ (e.g., airway tree) surface and ROIs, as well as the 3D paths. Local cross-sectional slices of the 3D data along and perpendicular to the endoscope viewing direction enable the physician to determine what lies between the tip of the scope and the ROI. This is useful for avoiding arteries and other organs when performing a biopsy.

RESULTS

The methods were incorporated into a computer GUI software package on a standard PC and have been tested with phantoms as well as live human subjects. For the phantom study, step-by-step results are presented for guidance to an ROI. For live human testing, a screen capture is presented from one of the 10 subjects for which this method was successfully used.

Phantom Study

Phantom results demonstrate that the guidance methods and system can be successfully used as a navigational aid to guide a physician to ROIs within a patient. The phantom used was a red ABS plastic rapid prototype model and was created from the endoluminal airway surfaces extracted from an MDCT scan of human patient 21405.3a. The MDCT scan was acquired by a 16-detector Siemens Sensation-16 scanner, and consists of 706 512×512 slices with resolution of $\Delta x = \Delta y = 0.67$ mm, $\Delta z = 0.5$ mm. Guidance was performed using an Olympus BF Type XP260F ultrathin bronchoscope with 2.8 mm distal tip diameter, and the bronchoscopic video was captured during the procedure by a Matrox Meteor-II video capture card at 30 frames per second. The video generated by this bronchoscope is circular and fits within a 288×290 pixel bounding box. Upon capture, the significant barrel distortion of the wide field-of-view (FOV) lens is corrected for each frame in real-time using the model of Zhang[39] and the distortion-corrected video is subsequently cropped to a rectangle measuring 292×313 pixels.

Figure 5:
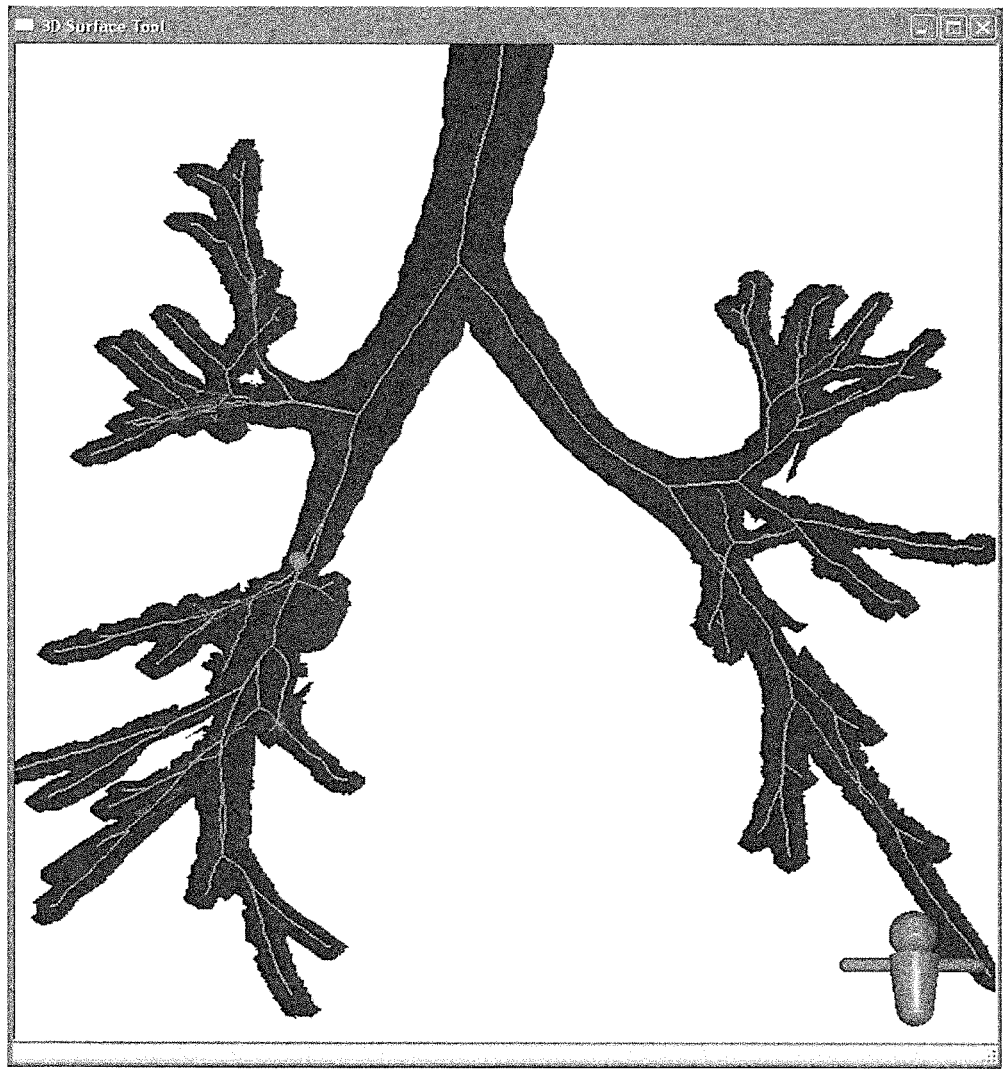
FIG. 5 shows a global external 3D surface rendering displaying the location of the ROI used for phantom testing.

Preoperative Planning and guidance were performed on a Dell Precision 650 workstation with a dual-core 3.0 Ghz Pentium processor, 4 GB RAM and 512 MB ATI Radeon video card, running Windows XP. All system software was built using Visual C++.NET 2003 and developed in-house. Prior to Phase-I Preoperative Planning by a physician, the endoluminal airway tree surfaces and centerlines were automatically extracted from the MDCT image. For this study, a spherical ROI was then defined manually, with 2.4 mm diameter and touching, but external to the endoluminal airway surfaces. The ROI—located between the right middle lobe takeoff and the right lower lobe—is displayed along with the endoluminal surfaces in FIG. 5. In clinical practice, this step would be performed by the physician. As a final automated Preoperative Planning step, the centerline path with closest approach to each ROI was computed and stored.[40] In FIG. 5, global external 3D surface rendering displays the location of the ROI used for phantom testing. The ROI resides at the bifurcation point between the right lower lobe and right middle lobe bronchi.

All Phase-I analysis and Phase-II guidance is performed using an integrated software system developed within our lab. The system consists of several interactive tools to manipulate and visualize the preprocessed anatomical dataset (raw 3D image, ROIs, endoluminal surfaces and centerlines, recorded snapshots and AVI movies, etc.) These tools include: multiplanar reformatted (MPR) slicers, useful for viewing, measuring and defining ROIs within the raw data; projection, sliding thin slab, oblique cross-section, shear-warp and volume renderers, useful for more complex visualization of the raw image data; endoluminal and extraluminal 3D surface renderers, providing visualization of endoluminal airway surfaces from the interior and exterior; and video match tools, providing the basis for guidance with the ability to register live endoscopic video with CT-derived endoluminal renderings. A more complete description of this system and its tools is provided by Higgins et at.[34]

During Phase-I analysis, the endoscopist views the location of the ROI on the transverse slicer as is standard practice, but is also presented with the extraluminal 3D surface renderer (e.g., FIG. 5), which provides an anatomical overview of each ROI's location. The endoscopist also plays an endoluminal fly-through movie along the path to each ROI, in order to preview the actual endoscopy.

Phase-II begins by interfacing the virtual endoscopy system with the endoscope. The virtual endoscopy software is then invoked, displaying the extraluminal renderer and the CT-Video matching tool, and the previously computed closest path is selected, which highlights this path in blue in both of these tools. At this point the video capture begins, providing the endoscopic video source for the CT-Video matching tool to process and display. For the ROI depicted in FIG. 5, each step along the path to the ROI is shown in FIG. 6. In each case, a 3D surface rendering displays the location of the VE camera within the endoluminal airway tree, while the RE video $I_{RE}^{\Theta_f}$ is displayed side-by-side with the VE view $I_{VE+P}^{\hat{\Theta}_f}$. Row 1, Left: The VE view $$I_{VE+P}^{\Theta_{v_0}}$$

is positioned near the main carina; Right: The endoscopist moves the RE camera to near the main carina. Row 2, Left: Registration/tracking is invoked at the main carina. The paths now appear overlaid on the RE view with $I_{RE}^{\Theta_f} \oplus I_P^{\hat{\Theta}_f}$ with the blue path highlighting the proper path to reach the ROI; Right: The VE view $I_{VE+P}^{\Theta_{v_1}}$ is moved to the second generation bifurcation. Row 3, Left: The endoscopist follows the path taken by the VE view to arrive at the same bifurcation; Right: A registration is performed, and the path again appears on the RE view $I_{RE}^{\Theta_f} \oplus I_P^{\hat{\Theta}_f}$. Row 4, Left: the VE view $$I_{VE+P}^{\Theta_{v_2}}$$

is moved to final bifurcation point; Right: Endoscopist follows the VE motion. Row 5, Left: A registration is performed, highlighting the location of the ROI on the RE view $I_{RE}^{\Theta_f} \oplus I_P^{\hat{\Theta}_f}$; Right: Continuous registration/tracking allows the 3D paths and ROI to move synchronously with the RE video view $I_{RE}^{\Theta_f} \oplus I_P^{\hat{\Theta}_f}$ as the physician moves the endoscope.

Initially, the VE view $I_{VE+P}^{\Theta_v}$ and the RE $I_{RE}^{\Theta_f}$ view are unregistered. As in step 1 of Strategy I, the VE view $I_{VE+P}^{\Theta_{v_0}}$ is moved to an easily identified initial location $\Theta_{v_0} = P^k(l_0)$ (just before the main carina in this case), as depicted in the left half of Row 1. Following step 2, the physician moves the endoscope to the vicinity of the VE view, depicted in the right half of Row 1. Per step 3, a registration is performed, bringing the VE view $I_{VE+P}^{\Theta_f}$ and RE video $I_{RE}^{\Theta_f}$ into alignment ($\Theta_v \leftarrow \hat{\Theta}_f$). This allows the fusion of path and ROI information $I_P^{\hat{\Theta}_f}$ from from the VE view onto the RE video data $I_{RE}^{\Theta_f}$ to form a fused RE view $I_{RE}^{\Theta_f} \oplus I_P^{\hat{\Theta}_f}$. This is shown on the left half of FIG. 6, Row 2. Because the correct path $P^k$ to reach the ROI is computed a priori and is overlaid on the RE video in blue, there is no ambiguity as to which direction to proceed. Proceeding to step 4, the VE camera is advanced along the path to the second bifurcation ($\Theta_v \leftarrow \Theta_{v_1} = P^k(l_1)$), beginning the second iteration of the process. Again, the physician follows the motion of the VE camera, and a registration is performed, as shown in Row 3 of FIG. 6. In Row 4, the VE camera is moved 1 bifurcation further down the path ($\Theta_v \leftarrow \Theta_{v_2} = P^k(l_2)$), and the physician again follows the motion of the virtual endoscope. At this point, the ROI (displayed in green) is clearly visible in the VE view $I_{VE+P}^{\Theta_{v_2}}$ at the bifurcation point.

Row 5 shows the result of registration, with the RE view $I_{RE}^{\Theta_f} \oplus I_P^{\hat{\Theta}_f}$, including superimposed paths and ROIs shown alongside the registered VE view $I_{VE+P}^{\hat{\Theta}_f}$. In this case, registration was allowed to proceed continuously as the endoscope was moved in real-time around the local region. As the scope is moved closer to the bifurcation point (right half of Row 5), the location of the ROI becomes very apparent with an icon indicating a possible approach to the ROI.

Human Studies

Figure 7:
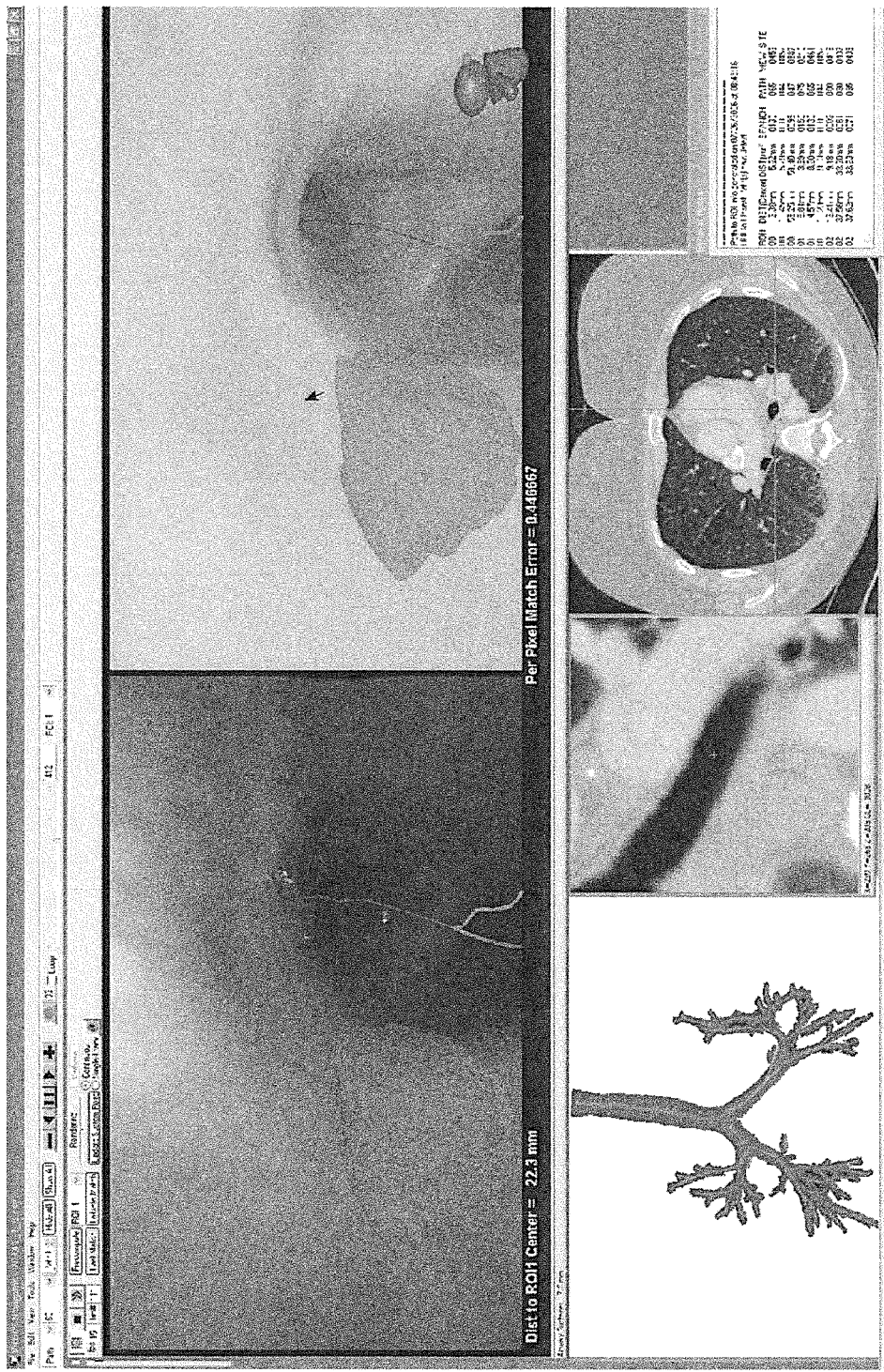
FIG. 7 is a screen capture of the image-based guidance system taken during a live bronchoscopy on a human patient.

In addition to phantom studies, this system has also been tested in ongoing live human tests using Strategies I and II for portions of each case. Ten such cases have been performed as of the submission of this paper and focus on bronchoscopic intervention of pulmonary patients using 3D chest CT. FIG. 7 is a screen capture taken during human case 20349.3.9, showing the layout of the overall virtual endoscopy system during a registration and just prior to a TBNA procedure. The bottom left window displays a global rendering of the tracheobronchial tree and ROIs, with the position and orientation of the bronchoscope tip shown by the sphere and needle. The appropriate path to the selected ROI is also shown. The CT-Video matching tool resides in the top window and displays the live bronchoscopic video feed on the left and the registered VE view on the right. Both views have the paths and ROIs transparently superimposed. The bottom center windows shows a cross-sectional view at the location of the endoscope tip, and is useful for determining what types of tissue lie beyond the airway walls that could potentially hinder biopsy. The window on the bottom right displays the transverse slice at the endoscope's current location and is similar to the radiologic slices a physician is accustomed to examining in standard practice.

DISCUSSION

This invention provides at least three integrated methods for continuous real-time image-based guidance of endoscopy. The methods build on each other and are not mutually exclusive; any combination of the methods may be used for guidance during an endoscopic guidance procedure. The framework presented is the first such paradigm to incorporate real-time 3D radiologic images and endoscopic video registration. This enables real-time guidance that provides the physician with continuously-updated precise navigational information.

The methods are a significant improvement over the current standard clinical workflow, which requires a physician to mentally reconstruct 3D structures from 2D transverse slices of the 3D scan data and later navigate to the ROIs with no guidance. The methods also improve upon past systems incorporating image-based registration. Single-frame registration has been reduced from several seconds to a fraction of a second, allowing a registration to appear instantaneous, as well as allowing registration to be performed much more frequently without extending the duration of the procedure. Furthermore, real-time registration enables new modes of image-based guidance not possible previously. Continuously registering the live video allows continuous updates to the VE view as well as the 3D paths and ROIs that are superimposed on both the VE and RE views.

Image-based registration/tracking also provides several advantages over existing E/M navigation systems. Image-based registration/tracking requires only a standard PC with a video capture card, while E/M registration requires special hardware that presents additional costs and typically limits the types of endoscopes that can be used. Further, E/M registration is sensitive to patient breathing or shifting motion during the procedure, as well as deformation of the organs due to different body position between the 3D scan and the procedure. These errors and the limited degrees of freedom some E/M sensors can detect make it difficult or impossible to present the physician with either the VE views or the superimposed 3D paths and ROIs corresponding to the current video frames.

REFERENCES

1. K. P. Wang and A. Mehta, eds., *Flexible Bronchoscopy*, Blackwell Science, Cambridge, Mass., 1995.
2. F. Tendick and M. C. Cavusoglu, "Human-machine interfaces for minnimally invasive surgery," in *Proceedings of the 19th Annual International Conference of the IEEE Engineering in Medicine and Biology Society*, 6, pp. 2771-2776, Oct. 30-Nov. 2 1997.
3. F. Reichenberger, J. Weber, M. Tamm, C. Bolliger, P. Dalquen, A. Perruchoud, and M. Soler, "The value of transbronchial needle aspiration in the diagnosis of peripheral pulmonary lesions," *Chest* 116(3), pp. 704-708, September 1999.
4. U. Topal and B. Ediz, "Transthoracic needle biopsy: factors effecting risk of pneumothorax," *Eur J Radiol* 48(3), pp. 263-267, December 2003.
5. S. Nazarian, B. P. Knight, T. L. Dickfeld, M. M. Zviman, V. B. Jayanti, D. Amundson, J. Hanlin, J. Castle-berry, M. F. Smith, L. Blankenship, H. R. Halperin, T. B. Ferguson, and R. D. Berger, "Direct visualization of coronary sinus ostium and branches with a flexible steerable fiberoptic infrared endoscope," *Heart Rhythm* 2(8), pp. 844-848, August 2005.
6. M. A. Tosca, A. M. Riccio, G. L. Marseglia, G. Caligo, E. Pallestrini, F. Ameli, E. Mira, P. Castelnuovo, F. Pagella, A. Ricci, G. Ciprandi, and G. W. Canonica, "Nasal endoscopy in asthmatic children: assessment of rhinosinusitis and adenoiditis incidence, correlations with cytology and microbiology," *Clin Exp Allergy* 31(4), pp. 609-615, April 2001.
7. J. D. Waye, D. K. rex, and C. B. Williams, eds., *Colonoscopy: Principles and Practice*, Blackwell Publishers, Malden, Mass., 2003.
8. P. Rogalla, J. Van Scheltinga, and B. Hamm, *Virtual Endoscopy and Related 3D Techniques*, Springer-Verlag, Berlin, 2002.
9. P. M. Boiselle, K. F. Reynolds, and A. Ernst, "Multiplanar and three-dimensional imaging of the central airways with multidetector CT," *Am. J. Roentgenology* 179, pp. 301-308, August 2002.
10. N. C. Dalrymple, S. R. Prasad, M. W. Freckleton, and K. N. Chintapalli, "Introduction to the language of three-dimensional imaging with multidetector CT," *Radiographics* 25(5), pp. 1409-1428, September-October 2005.
11. A. D. Sihoe and A. P. Yim, "Lung cancer staging," *J. Surgical Research* 117(1), pp. 92-106, March 2004.
12. D. Osborne, P. Vock, J. Godwin, and P. Silverman, "CT identification of bronchopulmonary segments: 50 normal subjects," *AJR* 142, pp. 47-52, 1984.
13. M. Y. Dolina, L. Buyantseva, S. A. Merritt, L. Rai, K. Lu, C. R. Cope, W. E. Higgins, R. P. Mahraj, M. Tucakovic, and R. Bascom, "Comparison of transverse chest CT images and a virtual navigation endoluminal imagge for bronchoscopy path selection to endoluminal pulmonary nodules," in *Proceedings of the American Thoracic Society*, p. A541, April 2006.
14. H. Minami, Y. Ando, F. Nomura, S. Sakai, and K. Shimokata, "Interbronchoscopist variability in the diagnosis of lung cancer by flexible bronchoscopy," *Chest* 105(2), pp. 1658-1662, June 1994.
15. E. F. Haponik, S. L. Aquino, and D. J. Vining, "Virtual bronchoscopy," *Clinics in Chest Med.* 20(1), pp. 201-217, March 1999.
16. V. Chechani, "Bronchoscopic diagnosis of solitary pulmonary nodules and lung masses in the absence of endobronchial abnormality," *Chest* 109(3), pp. 620-625, March 1996.
17. Y. Schwarz, A. C. Mehta, A. Ernst, F. Herth, A. Engel, D. Besser, and H. D. Becker, "Elecromagnetic navigation during flexible bronchoscopy," *Respiration* 70(5), pp. 515-522, September-October 2003.
18. S. B. Solomon, P. White, Jr., C. M. Wiener, J. B. Orens, and K. P. Wang, "Three-dimensionsal CT-guided bronchoscopy with a real-time electromagnetic position sensor: a comparison of two image registration methods," *Chest* 118(6), pp. 1783-1787, December 2000.
19. K. Mori, D. Deguchi, K. Akiyama, T. Kitasaka, C. R. Maurer, Y. Suenaga, H. Takabatake, M. Mori, and H. Natori, "Hybrid bronchoscope tracking using a magnetic tracking sensor and image registration," in *MICCAI* (2), J. S. Duncan and G. Gerig, eds., *Lecture Notes in Computer Science* 3750, pp. 543-550, Springer, 2005.
20. F. J. Herth, R. Eberhardt, and A. Ernst, "The future of bronchoscopy in diagnosing, staging and treatment of lung cancer," *Respiration* 73(4), pp. 399-409, 2006.
21. I. Wegner, M. Vetter, M. Schoebinger, I. Wolf, and H.-P. Meinzer, "Development of a navigation system for endoluminal brachytherapy in human lungs," in *Medical Imaging 2006: Visualization, Image-Guided Procedures, and Display*, J. Kevin R. Cleary, Robert L. Galloway, ed., 6141, pp. 23-30, March 2006.
22. F. Deligianni, A. Chung, and G. Yang, "Decoupling of respiratory motion with wavelet and principal component analysis," in *Medical Image Understanding and Analysis* 2004, pp. 13-16, September 2004.
23. H. P. McAdams, P. C. Goodman, and P. Kussin, "Virtual bronchoscopy for directing transbronchial needle aspiration of hilar and mediastinal lymph nodes: a pilot study," *Am. J. Roentgenology* 170, pp. 1361-1364, May 1998.
24. K. Hopper, T. Lucas, K. Gleeson, J. Stauffer, R. Bascom, D. Mauger, and R. Mahraj, "Transbronchial biopsy with virtual CT bronchoscopy and nodal highlighting," *Radiology* 221(2), pp. 531-536, November 2001.
25. N. Shinagawa, K. Yamazaki, Y. Onodera, K. Miyasaka, E. Kikuchi, H. Dosaka-Akita, and M. Nishimura, "CT-guided transbronchial biopsy using an ultrathin bronchoscope with virtual bronchoscopic navigation," *Chest* 125(3), pp. 1138-1143, March 2004.
26. J. P. Helferty, A. J. Sherbondy, A. Kiraly, and W. Higgins, "System for live virtual-endoscopic guidance of bronchoscopy," in *IEEE Conf. Computer Vision and Pattern Recognition*, 3, pp. 68-75, 20-26 June 2005.
27. B. Geiger, G. Weiner, K. Schulze, S. Bilger, P. Krebs, K. Wolf, and T. Albrecht, "Virtual bronchoscopy guidance system for transbronchial needle aspiration," in *SPIE Medical Imaging* 2005: *Physiology, Function, and Structure from Medical Images*, A. Amini and A. Manduca, eds., 5746, pp. 361-368, 2005.
28. I. Bricault, G. Ferretti, and P. Cinquin, "Registration of real and CT-derived virtual bronchoscopic images to assist transbronchial biopsy," *IEEE Transactions on Medical Imaging* 17(5), pp. 703-714, October 1998.
29. H. Shoji, K. Mori, J. Sugiyama, Y. Suenaga, J. Toriwake, H. Takabatake, and H. Natori, "Camera motion tracking of real endoscope by using virtual endoscopy system and texture information," in *SPIE Medical Imaging* 2001: *Physiology and Function from Multidimensional Images*, C. Chen and A. Clough, eds., 4321, pp. 122-133, 2001.
30. J. P. Helferty and W. E. Higgins, "Combined endoscopic video tracking and virtual 3D CT registration for surgical guidance," in *IEEE Conf. Image Processing*, 2, pp. II-961-II-964, Sep. 22-25 2002.
31. K. Mori, D. Deguchi, J. Sugiyama, Y. Suenaga, J. Toriwaki, C. R. Maurer, H. Takabatake, and H. Natori, "Tracking of bronchoscope using epipolar geometry analysis and intensity-based image registration of real and virtual endoscopic images," *Medical Image Analysis* 6, pp. 321-336, 2002.
32. F. Deligianni, A. Chung, and G. Yang, "pq-space based 2D/3D registration for endoscope tracking," in *Lecture Notes in Computer Science (MICCAI*2003), R. Ellis and T. Peters, eds., 2878, pp. 311-318, Springer-Verlag, 2003.
33. K. Mori, T. Enjoji, D. Deguchi, T. Kitasaka, Y. Suenaga, J. Toriwaki, H. Takabatake, and H. Natori, "New image similarity measures for bronchoscope tracking based on image registration between virtual and real bronchoscopic images," in *SPIE Medical Imaging* 2004: *Physiology and Function from Multidimensional Images*, A. A. Amini and A. Manduca, eds., 5369, pp. 165-176, 2004.
34. W. E. Higgins, L. Rai, S. A. Merritt, K. Lu, N. T. Linger, and K. C. Yu, "3D image fusion and guidance for computer-assisted bronchoscopy," in *SPIE Optics East: Three-Dimensional TV, Video, and Display IV*, B. Javidi, F. Okano, and J.-Y. Son, eds., 6016, pp. 86-100, November 2005.
35. J. P. Helferty, A. J. Sherbondy, A. P. Kiraly, and W. E. Higgins, "Computer-based system for the virtual-endoscopic guidance of bronchoscopy," in *Computer Vision and Image Understanding*, in press, 2006.
36. S. A. Merritt, L. Rai, and W. E. Higgins, "Real-time CT-video registration for continuous endoscopic guidance," in *SPIE Medical Imaging* 2006: *Physiology, Function, and Structure from Medical Images*, A. Manduca and A. A. Amini, eds., 6143, pp. 370-384, 2006.
37. L. Rai, S. A. Merritt, and W. E. Higgins, "Real-time image-based guidance method for lung-cancer assessment," in *IEEE Conf. Computer Vision and Pattern Recognition*, 2, pp. 2437-2444, June 2006.
38. L. Rai and W. E. Higgins, "Image-based rendering method for mapping endoscopic video onto CT-based endoluminal views," in *SPIE Medical Imaging* 2006: *Visualization, Image-Guided Procedures, and Display*, K. R. Cleary and J. R. L. Galloway, eds., 6141, pp. 1-12, 2006.
39. Z. Zhang, "Flexible camera calibration by viewing a plane from unknown orientations," in *ICCV*, pp. 666-673, 1999.
40. W. E. Higgins, K. Lu, S. A. Merritt, L. Rai, K. C. Yu, J. D. Gibbs, M. Y. Dolina, J. Toth, M. Tucakovic, and L. B. R. Bascom, "Virtual-bronchoscopic analysis of peripheral nodules," in *Proceedings of the American Thoracic Society, abstracts issue*, 3, p. A539, April 2006.

The invention claimed is:
1. A method for continuous guidance of endoscopy during a live procedure, comprising the steps of:
  a) providing a precomputed data-set based on 3D image data, the data-set including reference information representative of a predefined route through a body organ to a final destination, the reference information including virtual endoscopic (VE) image data representing one or more of the following: 3D organ surfaces, 3D routes through an organ system, and 3D regions of interest (ROIs);
  b) displaying a plurality of live real endoscopic (RE) images as an operator maneuvers an endoscope within the body organ;
  c) presenting information, corresponding to an initial reference location along the predefined route, which enables an endoscope operator to move the endoscope toward the reference location;
  d) invoking a registration/tracking algorithm that registers the VE image data to one or more of the RE images and continuously maintains the registration as the endoscope is locally maneuvered;
  e) presenting information corresponding to another reference location along the predefined route, which enables the endoscope operator to move the endoscope close to this new reference location;
  f) repeating steps d)-e) a plurality of times until the endoscope is within the vicinity of the final destination; and
  g) when the final destination is within the field of view of the endoscope, providing additional information enabling the endoscope operator to decide on a final maneuver for the procedure, the additional information including an icon, other the ROI itself, superimposed on at least one of the VE and RE images to visually indicate a direction from the final destination, including a visual indication of where to penetrate through the wall of the body organ, to the ROI.

2. The method of claim 1, including the step of superimposing one or both of the 3D routes and the ROIs on one or both of the RE and VE image data.

3. The method of claim 2, wherein one superimposed route is highlighted and continuously presented to guide the endoscope operator in steps c)-g).

4. The method of claim 3, wherein the registered VE view is displayed synchronously with the live RE video.

5. The method of claim 1, wherein the 3D organ surfaces correspond to the surfaces of a tracheobronchial airway tree extracted from 3D MDCT images of the chest.

6. The method of claim 1, wherein the 3D routes correspond to paths traversing a tracheobronchial airway tree extracted from 3D MDCT images of the chest or traversing other neighboring anatomical structures.

7. The method of claim 1, wherein the ROIs represent one tissue selected from the group consisting of lymph nodes and suspect tumors.

8. The method of claim 1, including the step of halting the registration/tracking algorithm prior to step e).

9. The method of claim 8, wherein a saved registration view is presented after halting the registration/tracking algorithm.

10. The method of claim 1, wherein step d) is done in real time.

11. The method of claim 1 wherein said introducing final maneuver information comprises rendering a portion of the body lumen wall semi-transparent to enhance visualization of the ROI on a display.

12. A system for continuous guidance of endoscopy during a live procedure, comprising:
 an endoscope maneuvered by an operator along a route to a final destination within a body organ;
 a display device operative to display live, real endoscopic (RE) images obtained by the endoscope;
 a memory storing a precomputed data-set derived from 3D image data, the data-set including reference information representative of a predefined route through a body organ to a final destination, the reference information including virtual endoscopic (VE) image data representing one or more of the following: 3D organ surfaces, 3D routes through an organ system, and 3D regions of interest (ROIs);
 a processor in communication with the memory and display, the processor being operative to:
 a) continuously register the VE image data to one or more of the RE images by displaying and updating the reference information as the operator maneuvers the endoscope, thereby continuously tracking the endoscope and guiding the operator to the final destination on the display device, and
 b) when the final destination is within the field of view of the endoscope, provide additional information enabling the endoscope operator to decide on a final maneuver for the procedure, the additional information including an icon, other than the ROI itself, superimposed on at least one of the VE and RE images to visually indicate a direction from the final destination, including a visual indication of where to penetrate through the wall of the body organ, to the ROI.

13. The system of claim 12, wherein one or both of the 3D routes and ROIs are superimposed on one or both of the RE and VE images.

14. The system of claim 13, wherein the processor is operative to highlight a superimposed route on the display as an operator maneuvers the endoscope.

15. The system of claim 14, wherein the VE view is displayed synchronously with the live RE video.

16. The system of claim 12, wherein the 3D organ surfaces correspond to the surfaces of a tracheobronchial airway tree extracted from 3D MDCT images of the chest.

17. The system of claim 12, wherein the 3D routes correspond to paths traversing the tracheobronchial airway tree extracted from 3D MDCT images of the chest or traversing other neighboring anatomical structures.

18. The system of claim 12, wherein the ROIs represent lymph nodes, suspect tumors, narrowed airways, or any other diagnostically relevant regions.

19. The system of claim 12, further including an operator control to halt the registration process.

20. The system of claim 19, wherein a saved registration view is presented on the display after halting.

21. The system of claim 12, wherein the registration is done in real time.

22. A method for guiding an endoscope through an airway to a ROI in a lung during a live procedure, comprising the steps of:
 a) receiving a virtual endoscopic (VE) image corresponding to a location along a precomputed route to said ROI;
 b) receiving a live real endoscopic (RE) image as an operator maneuvers an endoscope through said airway;
 c) superimposing said precomputed route onto at least one of said RE and VE images;
 d) registering said VE image to said RE image as the endoscope is maneuvered through said airway; and
 e) when the final destination is within the field of view of the endoscope, displaying information enabling the endoscope operator to decide on a final maneuver for the procedure, the information including an icon, other than the ROI itself, superimposed on at least one of the VE and RE images to visually indicate a direction from the final destination, including a visual indication of where to penetrate through the wall of the body organ, to the ROI.

23. The method of claim 22 wherein said final maneuver information comprises an icon superimposed in at least one of said VE and RE images.

24. The method of claim 23 wherein said icon is adapted to visually indicate a direction to the ROI from an end of the precomputed route.

25. The method of claim 24 wherein said icon is shaped as an arrow.

26. The method of claim 23 wherein said icon appears different as the endoscope moves relative to the ROI.

27. The method of claim 23 wherein said icon is representative of multiple final maneuver information.

28. The method of claim 27 wherein the multiple final maneuver information comprises a) direction and b) proximity to the ROI.

29. The method of claim 22 comprising providing a computer to perform each of said steps a) to e).

30. The method of claim 22 comprising repeating steps a) to d) until said endoscope is in the vicinity of the ROI.

31. The method of claim 22 wherein said preparing final maneuver information comprises rendering a portion of the airway wall semi-transparent to enhance visualization of the ROI on a display.

* * * * *